United States Patent [19]

Almen et al.

[11] 4,021,481
[45] May 3, 1977

[54] AMIDO DERIVATIVES OF 2,4,6-TRIIODOBENZOIC ACIDS CONTAINING AT LEAST ONE N-HYDROXYALKYL AND AT LEAST TWO HYDROXYL GROUPS

[75] Inventors: Torsten Almen; Johan Haavaldsen; Vegard Nordal, all of Oslo, Norway

[73] Assignee: Nyegaard & Co. A/S, Oslo, Norway

[22] Filed: Dec. 2, 1974

[21] Appl. No.: 528,842

Related U.S. Application Data

[63] Continuation of Ser. No. 301,101, Oct. 26, 1972, abandoned, which is a continuation-in-part of Ser. No. 50,075, June 26, 1970, Pat. No. 3,701,771.

[30] Foreign Application Priority Data

June 27, 1969 United Kingdom ............ 32699/69
Feb. 9, 1970 United Kingdom ............ 6130/70

[52] U.S. Cl. .................... 260/558 A; 260/490; 260/559 A; 424/5; 536/22
[51] Int. Cl.[2] ................ C07C 103/26; A61K 29/02
[58] Field of Search ....... 260/558 A, 558 D, 211 R, 260/518 A, 490, 559 A; 424/5

[56] References Cited

UNITED STATES PATENTS

| | | | |
|---|---|---|---|
| 2,820,814 | 1/1958 | Ginsberg | 260/471 |
| 2,921,884 | 1/1960 | Nachod et al. | 260/211 R X |
| 3,076,024 | 1/1963 | Larsen | 260/490 |
| 3,145,197 | 8/1964 | Hoey | 260/211 R |
| 3,360,436 | 12/1967 | Felder et al. | 424/5 X |
| 3,446,837 | 5/1969 | Wallingford | 260/562 R X |
| 3,452,134 | 6/1969 | Tilly | 424/5 |
| 3,476,802 | 11/1969 | Holtermann et al. | 260/518 |
| 3,574,718 | 4/1971 | Bjork et al. | 260/490 X |
| 3,622,616 | 11/1971 | Guerbet et al. | 260/471 R |
| 3,666,760 | 5/1972 | Ackerman | 260/518 A X |
| 3,886,203 | 5/1975 | Felder et al. | 260/490 X |
| 3,939,204 | 2/1976 | Buttermann | 424/5 X |
| 3,953,501 | 4/1976 | Klieger et al. | 424/5 X |

*Primary Examiner*—Daniel E. Wyman
*Assistant Examiner*—Thomas A. Waltz
*Attorney, Agent, or Firm*—Bacon & Thomas

[57] ABSTRACT

This invention relates to novel X-ray contrast agents particularly for use in the cerebrospinal cavities, comprising non-ionic alkanols carrying at least one N-bonded secondary or tertiary amide group and having at least two hydroxyl groups and at least one iodine atom in the molecule. Particularly useful compounds include the N-hydroxyalkyl iodoalkane sulphonamides having at least two hydroxyl groups, tri- and tetra-iodobenzene carrying carbamoyl, acylamino and/or acylaminomethyl substituents and having at least two hydroxyl groups in the molecule and at least one N-hydroxyalkyl group. Particularly preferred compounds comprise 2,4,6-triiodobenzamides which may be 3- and/or 5-substituted with a variety of groups. The compounds all show markedly low toxicities and a number show very high levels of water solubility.

9 Claims, No Drawings

AMIDO DERIVATIVES OF 2,4,6-TRIIODOBENZOIC ACIDS CONTAINING AT LEAST ONE N-HYDROXYALKYL AND AT LEAST TWO HYDROXYL GROUPS

This is a continuation of application Ser. No. 301,101 filed Oct. 26, 1972, now abandoned, which in turn is a continuation-in-part of application Ser. No. 50,075, filed June 26, 1970, now U.S. Pat. No. 3,701,771.

This invention relates to novel iodinated X-ray contrast agents.

In the X-ray visualisation of relatively extensive regions of the human body, for example the cardio vascular system or the space containing the cerebrospinal fluid, large quantities of quantities of X-ray contrast agents of high concentration have to be injected in order to provide sufficient opacity in the region concerned. Consequently, the toxicity of the contrast agent at high concentrations is of great importance. In the visualisation of the cardio vascular system a large number of compounds have been proposed as contrast agents and while many have been used successfully, their toxicity, although often very slight, does give rise to some undesirable side effects. In the visualisation of the space containing the cerebrospinal fluid, the highly concentrated compounds used in cardio vascular visualisation are frequently far too toxic, as is explained below.

The ideal contrast agent for the subarachnoideal space has not yet been found. Gases and oils have been proposed but have many disadvantages. The water soluble iodomethane sulphonate is the principal conventional contrast agent for this area, being of high opacity while being quite rapidly absorbed. This substance, however, is far from ideal; in visualising the various zones of the subarachnoideal space it is commonly used for radiculography but simultaneous application of an anaesthetic is necessary and it is too toxic for cisternography, ventriculography and cervical or thoracic myelography.

As indicated above, the iodinated compounds which are normally used in the cardiovascular system are usually chosen for their high solubility in water; solubilities of the order of 100 g/100 ml are common. In order to gain water solubility, compounds have usually been selected which carry an acidic group, for example a carboxylic acid or sulphonic acid group since their alkali metal salts and certain amine salts are frequently extremely water-soluble and while several commercially used contrast agents of this type exhibit extremely low levels of toxicity intravenously, their use at high concentrations has been found to lead to undesirable side effects when they are deposited in the cerebrospinal fluid. In addition to toxic effects due to the ions, it has been established that these side effects are due, in part, to the osmotic imbalance created by injecting very large concentrations of dissolved material into the body fluids.

The osmolality of a solution of a chemical compound is normally approximately directly proportional to the sum of the concentrations of the different molecular or ionic species which are present. A water-soluble salt, for example the sodium salt of an iodinated acid, will normally be almost completely ionised and the osmolality will be proportional to the concentration of both the anion and the cation. The total concentration of ionic species will thus be approximately twice that of the salt considered as a single unionised species. In contrast, the osmolality of a non-ionic compound, that is a compound which is substantially unionised in aqueous solution, is expected to be approximately proportional simply to the molarity of the compound present, that is approximately half the value for an analogous ionic compound having two ionic species.

In fact our investigations of osmolality have shown that the group of non-ionic compounds according to the invention defined more precisely below, show osmolality values considerably lower than those expected on the above basis.

We have now tested a number of non-ionic iodinated compounds and have verified that, in the particularly sensitive field of cerebrospinal visualisation, the toxicity of their concentrated aqueous solutions is generally very significantly lower than that of the best ionic compounds proposed for use in this application and in general is lower than that for the solutions of the corresponding ionic compounds.

Furthermore, many of the compounds exhibit intravenous toxicities markedly lower than those of the best commercial vascular contrast agents and hence are additionally valuable in cardio vascular visualisation.

Our studies have further led us to the conclusion that the iodinated compound should be an alkanol carrying at least one N-bonded secondary or tertiary amide group. In addition, the molecule should possess at least two hydroxyl groups.

According to the present invention therefore we provide as X-ray contrast agents, non-ionic alkanols carrying at least one N-bonded secondary or tertiary amide group and having at least two hydroxyl groups and at least one iodine atom in the molecule.

The N-bonded secondary or tertiary amide group in the new X-ray contrast agents may be derived, for example, from an aliphatic, araliphatic or aromatic carboxylic acid or sulphonic acid. Thus, for example, one class of compounds according to the invention are the N-hydroxyalkyl iodoalkane sulphonamides having at least 2 hydroxyl groups, e.g. mono- or di-iodomethane sulphonyl derivatives of amino alkanols such as mono- or dialkanolamines e.g. diethanolamine or amino sugars or sugar amino alcohols such as glucosamine, glucamine or N-methylglucamine. The amino alkanols preferably contain 2–6 carbon atoms in the alkanol groupings.

Yet another class includes the non-ionic tri- and tetra-iodobenzenes carrying carbamoyl, acylamino and/or acylamino-methyl substituents and having at least two hydroxyl groups in the molecule and at least one N-hydroxyalkyl group. The iodine atoms may be in any positions, preferably in the 2,4 and 6 positions.

One particularly preferred class of non-ionic X-ray contrast agents possesses the general formula

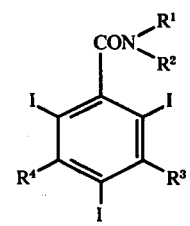

I where $R^1$ and $R^2$, which may be the same or differnt, are hydrogen atoms or alkyl, hydroxyalkyl or acyloxyalkyl groups and $R^3$ and $R^4$, which may be the same or different, are hydrogen atoms; acylamino groups of the formula NR⁵Ac, where $R^5$ is a hydrogen atom, an alkyl, hydroxyalkyl or acyloxyalkyl group or an acyl group and Ac is an acyl group; acylaminomethyl groups of the formula $CH_2NR^5Ac$, where $R^5$ and Ac have the above meanings; or carbamoyl groups of the formula $CONR^6R^7$, where $R^6$ and $R^7$ are hydrogen atoms or alkyl, hydroxyalkyl or acyloxyalkyl groups; there being at least one N-hydroxyalkyl group and at least 2 hydroxyl groups in the molecule.

Where the compounds of the invention carry carbamoyl groups, these are preferably mono- or di- alkyl and/or hydroxyalkyl carbamoyl groups advantageously having 1-6 carbon atoms in the alkyl portion. Acylamino groups which are preferred include lower aliphatic acylamino groups (advantageously those having 1-6 carbon atoms) which may carry as a further N-substituent an alkyl, hydroxyalkyl or acyloxyalkyl group.

The hydroxy alkyl groups which are present may carry a single hydroxy group, as in the β-hydroxyethyl group, or more than one hydroxy group as in the dihydroxypropyl or tris-(hydroxymethyl)-methyl group or in the polyhydroxyalkyl portion of hexosamines, pentosamines, and sugar aminoalcohols such as glucosamine or mannosamine or glucamines e.g. N-methyl glucamine, 1-glucamine or 2-glucamine. Other non-ionic substituents may also be present, for example the aldehyde group as present in glucosamine or one or more acyloxy groups.

The alkyl, hydroxyalkyl and aliphatic acyl groups which are present preferably contain 1-6 carbon atoms. Preferred alkyl groups thus include methyl, ethyl, propyl, butyl and hexyl groups; the methyl group is preferred and an N-methyl substituent often enhances water solubility.

The acyl group Ac may for example, be derived from a carboxylic acid or a sulphonic acid.

Preferred acyl groups derived from carboxylic acids, which may be O-attached or N-attached include acetyl, propionyl and butyryl groups, the acetyl group being most preferred. Preferred acyl groups derived from sulphonic acids include alkane sulphonyl groups such as the methane sulphonyl group.

The alkyl, hydroxyalkyl and acyl groups which are present may additionally carry a further non-ionic iodinated hydrocarbon grouping which may carry additional amide groups and, thus, for example, an alkylene, hydroxyalkylene or a diacyl grouping derived from a dibasic acid may be N-bonded at either end to identical iodinated hydrocarbons carrying amide groupings.

A number of compounds according to the invention which have been prepared are listed below in Table I

TABLE 1

| | |
|---|---|
| 1. | N-(3-N-methylacetamido-2,4,6-triiodobenzoyl)-glucamine |
| 2. | N-(3-diacetylamino-5-N-methylacetamido-2,4,6-triiodobenzoyl)-N-methylglucamine. |
| 3. | N-(N-methyl-3,5-diacetamido-2,4,6-triiodobenzoyl)-N-methyl glucamine. |
| 4. | N-[3-N-(β-hydroxyethyl)-acetamido-5-N-methylacetamido-2,4,6-triiodobenzoyl]-N-methyl-2,3-dihydroxypropylamine. |
| 5. | N-[N,N'-di-(β-hydroxyethyl)-3,5-diacetamido-2,4,6-triiodobenzoyl]-diethanolamine. |
| 6. | N-3-Acetamido-5-N-methylcarbamoyl-2,4,6-triiodobenzoyl)-N-methylglucamine. |
| 7. | N-(3-Acetamido-5-acetamidomethyl-2,4,6-triiodobenzoyl)-N-methylglucamine. |
| 8. | N-(3-N-methylbutyramido-2,4,6-triiodobenzoyl)-N-methyl-glucamine. |
| 9. | 3,5-Bis-[N-(2,3-dihydroxypropyl)-N-methylcarbamol]-2,4,6-triiodoacetanilite. |
| 10. | N-[3-N-(β-hydroxyethyl)-acetamido-5-N-methylacetamido-2,4,6-triiodobenzoyl]-glucosamine. |
| 11. | N-(N-methyl-3,5-diacetamido-2,4,6-triiodobenzoyl)-glucosamine. |
| 12. | N-[N,N'-di-(β-hydroxyethyl)-3,5-diacetamido-2,4,6-triiodobenzoyl]-glucosamine. |
| 13. | N-(3-N-butylacetamido-2,4,6-triiodobenzoyl)-N-methyl-glucamine. |
| 14. | N-(3,5-diacetamido-2,4,6-triiodobenzoyl)-glucosamine. |
| 15. | N-(N-methyl-3,5-diacetamido-2,4,6-triiodobenzoyl)-2-glucamine. |
| 16. | N-(3,5-diacetamido-2,4,6-triiodobenzoyl)-glucamine. |
| 17. | N-(3,5-diacetamido-2,4,6-triiodobenzoyl)-2-glucamine. |
| 18. | 3,5-Bis[N-(2',3'-dihydroxypropyl)-N-methylcarbamoyl]-N-(2'-hydroxyethyl)-2,4,6-triiodoacetanilide. |
| 19. | N-(3-acetamido-5-N-methylcarbamoyl-2,4,6-triiodo-benzoyl)-D-glucosamine. |
| 20. | N-(3-acetamido-5-N-methylcarbamcyl-2,4,6-triiodo-benzoyl)-D-2-glucamine. |
| 21. | N-(3-acetamido-5-N-methylcarbamoyl-2,4,6-triiodo-benzoyl)-D-1-glucamine. |
| 22. | N-(3-N-β-hydroxyethylacetamido-5-N-methylcarbamoyl-2,4,6-triiodobenzoyl)-D-glucosamine. |
| 23. | N-(3-N-β-hydroxyethylacetamido-5-N-methylcarbamoyl-2,4,6-triiodobenzoyl)-D-2-glucamine. |
| 24. | N-(3-N-β-hydroxyethylacetamido-5-N-methylcarbamoyl-2,4,6-triiodobenzoyl)-D-1-glucamine. |
| 25. | N-(3,5-diacetamido-2,4,6-triiodobenzoyl)-N-methyl-glucamine. |
| 26. | N-(2,4,6-triiodobenzoyl)-N-methylglucamine. |
| 27.(a) | 3,3'(Adipoyl-dimino)-bis-[N-(2,4,6-triiodobenzoyl)-diethanolamine], and (b) the corresponding N-methyl glucamine derivative |
| 28. | N-(Iodomethane sulphonyl)-N-methylglucamine. |
| 29. | N-(Iodomethanesulphonyl)-diethanolamine. |
| 30. | N-(3-acetamido-2,4,6-triiodobenzoyl)-N-methyl-glucamine. |
| 31. | N-(3-N-methylacetamido-2,4,6-triiodobenzoyl)-N-methylglucamine. |

TABLE 1-continued

| | |
|---|---|
| 32. | N-(3-N-methylacetamido-2,4,6-triodobenzoyl)-D-glucosamine. |
| 33. | N-(N-methyl-3,5-diacetamido-2,4,6-triiodobenzoyl)-D-glucamine. |
| 34. | N-(N-methyl-3,5-diacetamido-2,4,6-triiodobenzoyl)-N,N-di-(β-hydroxyethyl)-amine. |
| 35. | N-[3-N-methylacetamido-5-N-(β-hydroxyethyl)-acetamido-2,4,6-triiodobenzoyl]-N-methylglucamine. |
| 36. | N-[3-N-methylacetamido-5-N-(β-acetoxyethyl)-acetamido-2,4,6-triiodobenzoyl]-N-methylglucamine. |
| 37. | N-[3-N-methylacetamido-5-N-(β-hydroxyethyl)-acetamido-2,4,6-triiodobenzoyl]-ethanolamine. |
| 38. | N-[3-N-methylacetamido-5-N-(β-hydroxyethyl)-acetamido-2,4,6-triiodobenzoyl]-N-methylethanolamine. |
| 39. | N-[3-N-methylacetamido-5-N-(β-hydroxyethyl)-acetamido-2,4,6-triiodobenzoyl]-diethanolamine. |
| 40. | N-[3-N-methylacetamido-5-N-(β-hydroxyethyl)-acetamido-2,4,6-triiodobenzoyl]-N-(2,3-dihydroxypropyl)-amine. |
| 41. | N-[3-N-methylacetamido-5-N-(β-hydroxyethyl)-acetamido-2,4,6-triiodobenzoyl]-N-[tris-(hydroxymethyl)-methyl]-amine. |
| 42. | N-[3-N-methylacetamido-5-N-(2,3-dihydroxypropyl)-acetamido-2,4,6-triiodobenzoyl]-N-methylglucamine. |
| 43. | N-[3,5-bis-N-(β-hydroxyethyl)-acetamido-2,4,6-triiodobenzoyl]-N-methylglucamine. |
| 44. | N-3,5-bis-N-(β-hydroxyethyl)-acetamido-2,4,6-triiodobenzoyl]-N-methyl-N-(2,3-dihydroxypropyl)-amine. |
| 45. | N-[3,5-bis-N-(β-hydroxyethyl)-acetamido-2,4,6-triiodobenzoyl]-ethanolamine. |
| 46. | 3,5-bis[N-di(β-hydroxyethyl)-carbamoyl]-2,4,6-triiodoacetanilide |
| 47. | 3,5-bis-[N-(2',3'-dihydroxypropyl)-carbamoyl]-2,4,6-triiodoacetanilide. |
| 48. | N-(N-methyl-3,5-diacetamido-2,4,6-triiodobenzoyl)-manrosamine. |
| 49. | N-(3-Acetamido-5-N-methylcarbamoyl-2,4,6-triiodobenzoyl)-N-(2-hydroxyethyl)-glucamine |

As indicated above, the new non-ionic compounds according to the invention have shown markedly low levels of toxicity, especially in intracerebral tests. Table 2 below shows results obtained for a number of compounds according to the invention, as compared with previously known X-ray contrast agents. It will be seen that all the new compounds listed are very much better than the known compounds in the intracerebral test.

TABLE 2

Intravenous and Intracerebral Toxicity in Mice

| Compound No. (see Table 1) | Intravenous | | Intracerebral | | |
|---|---|---|---|---|---|
| | $LD_{50}$ mgl/kg | Concentration administered mgl/ml | $LD_{50}$ mgl/kg | Concentration administered mgl/ml | Dose ml/20 g mouse |
| 3 | 6000 | 300 | >750 | 300 | 0.05 |
| 33 | 14250 | 300 | >750 | 300 | 0.05 |
| | | | >1500 | 300 | 0.10 |
| 35 | | | >750 | 300 | 0.05 |
| | | | >2000 | 400 | 0.10 |
| 4 | | | >1000 | 400 | 0.05 |
| 10 | 8250 | 300 | >750 | 300 | 0.05 |
| | | | >1500 | 300 | 0.10 |
| 43 | 7500 | 300 | >1000 | 400 | 0.05 |
| | | | >2000 | 400 | 0.10 |
| 44 | | | >750 | 300 | 0.05 |
| | | | >1500 | 300 | 0.10 |
| 6 | 10000 | 300 | >1500 | 300 | 0.10 |
| 9 | 13500 | 300 | about 1500 | 300 | 0.10 |
| 11 | 15000 | 300 | >1500 | 300 | 0.10 |
| 12 | >12000 | 300[a] | >1500 | 300 | 0.10 |
| 15 | >15000 | 300[b] | >1500 | 300 | 0.10 |
| 49 | 15000 | 300 | >1500 | 300 | 0.10 |
| Iodomethanesulphonic acid | | | 195 | | 0.05 |
| N-Methyl-3,5-diacetamido-2,4,6-triiodobenzoic acid | 6000[x] | 280 | 130 | | 0.05 |
| 5-Acetamido-2,4,6-triiodo-N-methyliso-phthalamic acid | 6000[x] | 280 | 210 | | 0.05 |

[x]N-methylglucamine salt.
[a]Dose: 0.8 ml/20 g mouse
[b]Dose: 1.0 ml/20 g mouse Most of the compounds were so inert that it was not physically possible to inject sufficient substance to kill 50% of the mice and in such cases only a minimum value can be given for the $LD_{50}$.

A number of the new compounds are distinguished by very high levels of water solubility. These are shown in Table 3 below.

TABLE 3

| Definitions: | Solubility in water at room temperature | | | |
|---|---|---|---|---|
| | High | = | solubility 50% | (w/v) |
| | Medium | = | " 20 – 50% | " |
| | Low | = | " 20% | " |

| Compound No. | |
|---|---|
| 1 | High |
| 3 | High |
| 4 | High |
| 5 | High |
| 6 | High |
| 7 | High |
| 9 | High |
| 10 | High |
| 11 | High |
| 12 | High |
| 14 | High |
| 15 | High |
| 25 | Low (7.9%) |
| 30 | High |

TABLE 3-continued

| | Solubility in water at room temperature | |
|---|---|---|
| Definitions: | High = lubility 50% | (w/v) |
| | Medium = " 20 – 50% | " |
| | Low = " 20% | " |
| 31 | High | |
| 32 | High | |
| 33 | High | |
| 34 | Medium (21.3%) | |
| 35 | High | |
| 36 | Medium | |
| 37 | Low (0.40%) | |
| 38 | Medium (25.5%) | |
| 39 | High | |
| 40 | Low (0.26%) | |
| 41 | Low (0.86%) | |
| 43 | High | |
| 44 | High | |
| 45 | Medium (21.4%) | |

It will further be seen that those compounds shown in Table 3 having 3 or more hydroxyl groups are, except where a secondary amide or ester group is present, highly water soluble and are generally preferred.

It should be noted, however, that while high water solubility is for many purposes desirable in an X-ray contrast agent, it is not essential and compounds having very low toxicity levels may be useful even when they are water-insoluble.

As indicated above, the compounds according to the invention are of low osmolality as compared to conventional ionic contrast agents and many of the compounds show even lower osmolality values than would have been expected. The observed osmolality in each case would be expected to be about 0.8 mol/kg but compounds 3, 33, 35, 44 and 11 identified in Table I have shown osmolality values of 0.47, 0.48, 0.61, 0.53 and 0.48 mol/kg respectively at 37° C (300 mg I ml). The last two compounds in Table 2, which are ionic compounds shown for comparison, have osmolality values of about 1.6 mol/kg.

In general, the compounds which are most preferred as contrast agents in the myclographic field include Compounds 6, 9, 10, 11, 12, 15 and 33 from Table I.

Those compounds which are highly water-soluble and possess acceptable viscosities are also useful as cardiovascular contrast agents and compound 9 in Table 1 above is especially useful in this respect, having a viscosity of 7.1 cp at 20° C and a concentration of 300 mgI/ml. However, the preferred compounds listed above in relation to the myelographic field are also very useful in cardiovascular visualisation due to their extremely good tolerance.

According to a further feature of the present invention we provide a radiological composition containing at least one non-ionic compound according to the invention together with a radiological carrier.

The concentration of the X-ray contrast agent according to the invention in the aqueous medium for administration varies with the particular field of use. In general lower concentrations are required for ventriculography than for myelography while radiculography requires still lower concentratons. The preferred concentration and dosage ranges of the compounds for these three applications are as follows:

| | Concentration | Dose |
|---|---|---|
| Radiculography | 150 – 250 mg I/ml | 6 – 12 ml |
| Ventriculography | 250 – 350 mg I/ml | 3 – 7 ml |
| Myelography | 350 – 450 mg I/ml | 4 – 9 ml |

The preferred concentration range for cardiovascular visualisaton is 150 – 450 mg I/ml. The quantity of contrast agent to be administered is preferably such as to stay in the system only for about 2 to 3 hours, although both shorter and longer residence periods are normally acceptable. The active material may thus be formulated for cerebrospinal visualisation conveniently in vials or ampoules containing 5 to 15 ml of an aqueous solution thereof, but for vascular visualisation larger quantities e.g. 10 to 500 ml will be given.

The new compounds according to the invention can be prepared in any convenient way. The following methods are of especial interest and constitute further features of the invention.

1. Reaction of a carboxylic or sulphonic acid having at least one iodine atom or an amide-forming derivative thereof with an amine or ammonia whereby a non-ionic amide is produced having at least one N-hydroxyalkyl group, at least two hydroxyl groups and at least one iodine atom in the molecule.

In particular, this method includes reaction of a compound of the general formula

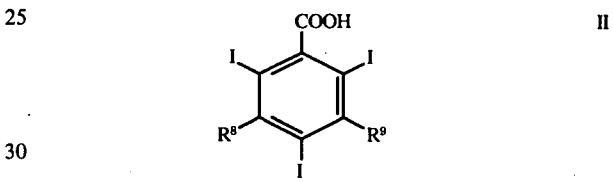

(where $R^8$ and $R^9$ which may be the same or different have the meanings given above for $R^3$ and $R^4$ or are carboxyl groups) or an amide forming derivative thereof, with a compound of the formula $HNR^1R^2$ (where $R^1$ and $R^2$ have the meanings given above). The preferred method of effecting this reaction is to condense an acid halide, e.g. the bromide or, more advantageously the chloride, with the compound of formula $NHR^1R^2$. The reaction is preferably effected in an inert solvent such as a cyclic ether, e.g. dioxan or tetrahydrofuran, or an amide solvent such as dimethyl formamide or dimethylacetamide. A slight excess of the amine is advantageously used and an acid binding agent may be present, for example an alkali metal carbonate or bicarbonate or a tertiary amine such as triethanolamine. A suitable excess of amine can, however, serve as acid binding agent or, when liquid, as solvent.

For the isolation of the carbamoyl compounds the residue from the evaporated reaction mixture may be dispersed in water and acid of formula II regenerated by hydrolysis of acid halide may be dissolved by addition of alkali. Where it is wished to remove acyl groups used to protect hydroxyl groups of NH-groupings during the formation of the acid halide, the treatment with alkali may be performed at elevated temperature, e.g. 50°–60° C. The less water-soluble carbamoyl compounds may be separated from such aqueous solutions. Where more water-soluble carbamoyl compounds are concerned, however, separation from inorganic salts, for example those formed between the acid binding agent and the liberated hydrogen halide or those formed by neutralisation of the acid halide, proves difficult. Under such circumstances, the water soluble carbamoyl compound can be isolated by, for example, phenol extraction.

Thus, the residue from the reaction mixture may be dissolved in water and, if necessary, treated with alkali as described above, whereupon the solution is made acid, for example by addition of a mineral acid such as hydrochloric acid, e.g. to about pH$^1$ and extracted with phenol. The phenol extracton is preferably carried out in a number of separate extractions, for example 3 or 4, and the phenol extracts combined. Each phenol extract is advantageously 1/10 to 1/5 of the aqueous volume. The phenol is preferably 90% aqueous phenol. The combined phenol extracts are then washed several times, for example 3–5 times, with water to extract remaining inorganic salts, and about 2–3 volumes of ether ae added. The phenol/ether solution is then extracted with water, preferably several times, e.g. 3–5 times, using 1/10 volume of water for each extraction. The aqueous solution is then washed with ether to remove residual phenol and evaporated to dryness to yield the desired contrast agent. It is also possible to purify water soluble contrast agents by contacting the reaction solution with ion exchange resins, e.g. cation exchange resins to remove cations from the acid binding agent and/or anion exchange resins to remove the acid from the hydrolised acid halide.

The products may also be isolated by extraction of the reaction mixture e.g. with cyclic ethers such as tetrahydrofuran or dioxan.

The acid halides of the acids of formula II, which are themselves novel compounds, can be prepared by reaction of the acid with a halogenating reagent such as thionyl chloride or bromide, phosphorus pentachloride or bromide or phosphorus oxychloride or oxybromide. An inert solvent, for example a cyclic ether such as dioxan or tetrahydrofuran or a hydrocarbon solvent such as benzene or toluene may be used or an excess of the reagent may serve as reaction medium. Where there are free NH and/or OH present in the starting acid, however, these may react with the halogenating agent and in such cases are preferably protected. Acylation is the most convenient form of protection since both N-acyl and O-acyl groups may be added simultaneously by reaction with an acylating agent such as an acyl halide or anhydride. The acyl groups are preferably aliphatic acyl groups such as propionyl or, more preferbly, acetyl groups. The hydroxyl groups on sugar or sugar alcohol residues can also be protected for example by ketal formation.

One particularly suitable class of protecting groups are the trialkylsilyl groups e.g. the trimethylsilyl group. All the free hydroxyl groups of the hydroxy-amine reactant can conveniently be protected simultaneously in this way, e.g. by reaction with a trialkylsilyl halide, for example the chloride, preferably at low temperatures, e.g. 0°–20' C, to avoid formation of N-derivatives; tertiary amines such as pyridine are particularly suitable solvents and serve also as acid binding agents. An inert solvent such as an ether may additionally be present.

As indicated previously, these protecting groups can be allowed to remain during amide formation but may be removed thereafter by hydrolysis.

The trialkylsilyl protecting groups can be removed subsequently by hydrolysis with dilute acid, for example an aqueous alcoholic solution of hydrochloric acid at pH 2–3. It is also possible to form the acid halides by halogenation of acids of formula II having no hydroxyalkyl groups and to introduce these groups subsequently e.g. by the methods described below.

The iodinated sulphonic acid derivatives e.g. iodomethanesulphonyl derivatives according to the invention may be prepared by reaction of a corresponding sulphonyl halide e.g. an iodomethanesulphonyl halide, for example the chloride, with a suitable hydroxyamine. Since the sulphonyl halide may in some cases react both with the NH grouping and the hydroxy groups which the amine carries, the latter should in such cases be protected selectively before the reaction as described above. This is particularly required in preparing derivatives of amino-sugars or sugar alcohols such as N-methyl glucamine.

The sulphonylation may be carried out in an inert solvent, preferably an ether such as dioxen, tetrahydrofuran or dimethoxyethane; an acid binding agent is preferably present for example a tertiary amine such as pyridine or a trialkylamine e.g. triethylamine. The reaction is preferably effected at low temperature e.g. 0°–20° C.

2. Reaction of a non-ionic amide having at least one iodine atom with an alkylating, acyloxyalkylating or hydroxyalkylating agent whereby a non-ionic amide is formed having at least one N-hydroxyalkyl group, at least two hydroxyl groups and at least one iodine atom in the molecules. This method includes in particular

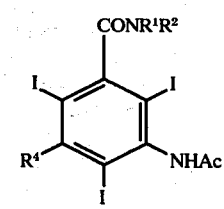

III (where R$_1$, R$^2$, R$^4$ and Ac have the above meanings) with an alkylating, acyloxyalkylating or hydroxyalkylating agent. The "alkylating" agent may, for example, be a reactive-mono-ester derivative of an alcohol or polyol, for example a halide, e.g. a chloride or bromide, or a sulphate or hydrocarbon-sulphonate. For the introduction of a hydroxyethyl group, 2-chloroethanol is one suitable reagent. For introducing a methyl group, dimethyl sulphate is a suitable reagent. The reactive derivative is preferably reacted with the acylamido starting material under basic conditions, e.g. in an aqueous alkaline medium, for example containing an alkali metal hydroxide such as sodium or potassium hydroxide or in a non-aqueous medium, e.g. in an alkanol such as methanol or ethanol, the base conveniently being an alkali metal alkoxide such as sodium methoxide. It is also possible to react the acylamido compound with an epoxide, for example ethylene oxide, propylene oxide, glycide etc., advantageously in neutral alcoholic solution.

3. Reaction of an iodinated amide as defined in (2) above and having an NH grouping, e.g. a carbamoyl compound of formula III, with an allylating agent, e.g. a reactive ester of an allylic alcohol, for example allyl chloride or bromide, to introduce an N-allylic grouping which is then subjected to oxidation of the double bond thereof, e.g. using a permanganate oxidising agent, to form a glycol grouping, whereby a non-ionic amide having an N-dihydroxy alkyl group is formed, e.g. a compound of formula I in which R$^1$ is a dihydroxy alkyl group such as a dihydroxypropyl group.

4. Reaction of a non-ionic amide having at least one iodine atom, at least one N-hydroxyalkyl group and at least one NH grouping with an acylating agent followed by hydrolysis of any unwanted acyloxy groups formed in the reaction.

This method thus particularly includes reaction of a compound of the formula

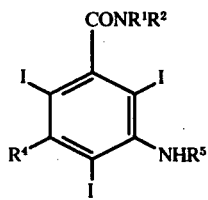

IV with an acylating agent followed by hydrolisis of any unwanted acyloxy groups formed in the reaction.

The acrylating agent, may, for example, be an acid anhydride (which can also serve as solvent) together with catalytic amounts of a mineral acid, e.g. sulphuric or perchloric acid, or an acid halide preferably in a polar solvent such as dimethyl-formamide or dimethyl-acetamide, acid halides being preferred due to smaller amounts of by-products formed. The basic hydrolysis of the O-acyl grouping may for example, be effected using aqueous alkali metal hydroxide e.g. sodium hydroxide, the reaction preferably being carried out at room temperature. In addition, depending on the acylating agent used, other products may be formed and require separation. When an acyl anhydride such as acetic anhydride is used with concentrated sulphuric acid as catalyst, a primary amino group is often, in part, bis-acylated, although the bis-acylamino group is very readily hydrolysed to acylmide under mild basis conditions.

5. Iodination of a benzoic acid amide carrying at least one N-hydroxyalkyl group and having at least two hydroxyl groups in the molecule whereby at least one iodine atom is introduced. The iodination may conveniently be effected using iodine monochloride or a complex thereof such as sodium iododichloride. The reaction is preferably effected in an aqueous medium, advantageously at acid pH.

The benzoic acid amide used as starting material may carry other groups in the molecule but at least one, and preferably all three, of the 2-, 4- and 6- positions should be unsubstituted. The 3- and/or 5- positions may, for example, carry the groups $R^3$ and $R^4$ as defined above in relation to formula I but at least one free $NH_2$ group is preferably present.

Thus, for example, a 3,5-diamino-benzoic acid amide carrying an N-hydroxyalkyl group and having at least two hydroxyl groups may be reacted with an iodinating reagent whereby iodine atoms can be introduced at the 2-, 4- and 6- positions, the free $NH_2$ groups subsequently being converted into acylamino groups by acylation, e.g. using acylating agents such as acid anhydrides or halides.

The 3,5-diamino-benzoic acid amide may be prepared by reduction of the corresponding 3,5-dinitro-benzoic acid amide or 3-amino-5-nitro-benzoic acid amide, using reagents serving to reduce a nitro group to an amino group, for example catalytic hydrogenation, e.g. using a palladium catalyst; hydrazine and Raney-nickel; or reaction with a source of sulphite, bisulphite ordithionite ions, e.g. sulphur dioxide or an alkali metal sulphite, bisulphite or dithionite in an aqueous medium, to yield a sulphamino group, $NHSO_3H$, followed by hydrolysis to yield an $NH_2$ group (Piria reaction) e.g. using a mineral acid such as hydrochloric acid. The sulphamino compound may, however, be reacted if desired, with an alkylating hydroxyalkylating or acyloxyalkylating agent before hydrolysis, whereby an alkylamino, hydroxyalkylamino or acyloxyalkylamino group is produced.

The amide starting compound may be prepared by a method analogous to (1) above.

The foregoing iodination reaction can, of course, be effected on free benzoic acids or reactive derivatives thereof, such as halides or esters, to produce starting materials for reaction (1).

The compounds of formula I, and in particular those in which $R^3$ represents the grouping $NR^5AC$, are subject to a number of different types of isomerism as is explained below. The present invention extend to all of these isomeric forms. Referring to the following formula

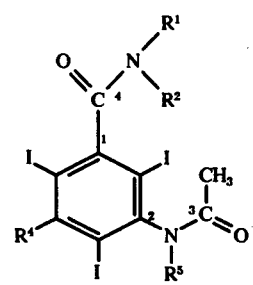

and the bonds numbered 1 – 4 therein, the following forms of isomerism can be distinguished:

a. Exo-endo isomerism due to restricted rotation of the N—CO bond (3) caused by steric hindrance from the adjacent bulky iodine atoms. These isomers tend to equilibrate in solution but are sufficiently stable to be separated by thin layer chromatography and, for example, the glucosamide of N-methyl-3,5-bis-acetamido-2,4,6-triiodobenzoic acid consists of about 20% of the endo form and 80% of the exo form. $R^5$ must be other than hydrogen for such isomerism to exist b. Cis-trans isomerism due to restricted rotation of the bonds (1) and (2), again caused by steric hindrance from the adjacent iodine atoms. It is necessary that none of $R^1$, $R^2$ and $R^5$ is hydrogen for this type of isomerism to exist. While the bond 2 does not appear to allow any rotation, equilibration of the bond 1 appears to be more facile and cis-trans isomers have not been separated up to the present time.

c. Syn-anti isomerism due to restricted rotation of the C—N bond (4). Naturally $R^1$ and $R^2$ must be different and other than hydrogen. The resistance to rotation of the bond (4) is similar to that of the bond (3) but no chromatographic separation has been effected up to the present time.

Where the group —$NR^1R^2$ constitutes the residue of a sugar amine, two further types of isomerism exist, namely:

d. Geometrical isomerism of the hemi-acetal bond in the cyclic sugar form. Mutarotation is possible so that although one form may be in excess when the amide is crystallised under neutral or basic conditions, acids leads to a proton catalysed equilibration. In consequence, when optical rotation is determined in order to characterise a sugar amide, the product should preferably first be equilibrated in acid in order to obtain a characteristic value not dependent on the presence of an excess of one hemi-acetal isomer.

e. Optical isomerism due to the optical characteristics of the sugar amine. In general, the D-forms of the sugar amines have been used in the present work but L-forms can equally be used. This type of isomerism exists, of course, whenever an asymmetric carbon atom is present and the sugar alcohol amides also exist in the D- or L- form. Again, the D-forms have in general been used.

Where the group $NR^1R^2$ is derived from glucosamine, a still further type of isomerism is possible, namely:

f. Glucose-mannose epimerism. Glucosamides can undergo epimerism at the carbon atom adjacent to the aldehyde group present in the open chain form which always coexists in equilibrium with the cyclic form. This epimerisation is catalysed by hydroxyl ions and produces the corresponding mannoside. In syntheses of glucosamides under alkaline conditions a proportion of mannoside will therefore usually be present in the initial reaction mixture and can be separated by thin layer chromatography. For practical use of the X-ray contrast compound, however, such separation may not be necessary.

The acids of formula II are, in many cases, known compounds. Others are described in our Belgian Patent No. 734257. The carbamoyl compounds of formula III may, in fact, be obtained from the corresponding acids, by the method (1) above.

The highly water-soluble compounds according to the invention, by virtue of their high molecular weight, are able to dissolve to give solutions of very high specific gravity. Such solutions are especially useful in biological techniques whereby cells are handled in solutions of high specific gravity, for example in centrifugation or differential flotation, because their low osmolality reduces the osmotic layers of the cells which is found when concentrated solutions of salts are used for that purpose.

Preparations a. Starting materials 1. 3-Amino-5-N-methylacetamido-2,4,6-triiodobenzoylchloride 3-Amino-5-N-methylacetamido-2,4,6-triiodobenzoic acid (586 g, 1.0 mol) was suspended in thionyl chloride (596 ml) and reacted by stirring at 70° C for 16 hours. Excess thionyl chloride was distilled off in vacuo, the residue dissolved in chloroform (2500 ml) cooled in the ice-bath, washed with iced water (3 × 100 ml), saturated $NaHCO_3$ solution (3 × 100 ml) 2N $Na_2CO_3$ solution (2 × 100 ml) and finally with water (3 × 100 ml). After drying with $CaCl_2$ the chloroform was distilled off and the residue dried in vacuo. Yield: 522 g (91%); m.p. 145° – 160° C. A sample was crystallized from ethyl acetate. M.p. 181° – 205° C. Found: Cl 5.37; Calcd. for $C_{10}H_8CII_3N_2O$: Cl 5.88.

2. 3-Amino-5-N-methylacetamido-2,4,6-tiiodobenzyl chloride prepared by using $PCl_5$ 3-Amino-5-N-methylacetamido-2,4,6-triiodobenzoic acid (58.6 g; 0.1 mol) was suspended in toluene (50 ml) and benzene (25 ml). The benzene was distilled off in order to remove traces of water. Phosphorus pentachloride (20.8 g; 0.1 mole) was added by stirring at 40° and then heated to 70° C and stirred for 16 hours. The new crystalline compound precipitated before all starting material was dissolved. The reaction mixture was stored at −20° before filtration. Yield: 52.9 g (87%). Found: Cl. 5.78. Calcd. for $C_{12}H_{10}CII_3H_2O_3$: Cl 5.88.

3. a. 3-Diacetylamino-5-N-methylacetamido-2,4,6-triiodobenzoyl chloride

The acid chloride from Preparation 2 (80 g) was suspended in acetic anhydride (400 ml) and heated to 60° C. $H_2SO_4$ conc. (0.16 ml) was added by stirring and the reaction mixture was stirred at 100° C for 2 hours and at room temperature overnight. The filtered product was suspended in glacial acetic acid, refiltered and dried. Yield: 77 g (85%); m.p. 255°–260° C. Crystallised from dioxan the compound melted at 261° – 265° C. Found: C 24.84; H 2.12; N 4.10; Cl 5.2. Calcd. for $C_{14}H_{12}CII_3N_2O_4$: C 24.43; H 1.76; N 4.07; Cl 5.15.

b. When the acetylation was performed with crude acid chloride and at room temperature only one acetyl group was introduced. Yield: 66%; m.p. 238° – 240° C (tetrahydrofuran). Found: Cl 5.41. Calcd. for $C_{12}H_{10}CII_3N_2O_3$: Cl 5.49.

4. 3-N-($\beta$-Acetoxyethyl)-acetamido-5-N-methylacetamido-2,4,6-triiodobenzoic acid 3-N-($\beta$-Hydroxyethyl)-acetamido-5-N-methylacetamido-2,4,6-triiodobenzoic acid (268 g, 0.4 mol) was added in portions to dry pyridine (500 ml) by stirring. The solution was heated to 50° C and acetic anhydride (80 ml, 0.8 mol) was added in drops in the course of 30 min. The stirring was continued for 1 hour whereafter the pyridine was distilled of in vacuo. The residual oil was dissolved in water (1000 ml), charcoaled at room temperature, filtered and the O-acetylated product precipitated with 6N HCl to pH 1.5. The acid was filtered after stirring at room temperature for 16 hours and dried in vacuo at 70+ C.

Yield: 235.4 g (82.5%), m.p. 194°–199° C. Crystallized from dioxan m.p. 199° – 201° C. Found: C 26.84; H 2.54; N 4.01. Calcd. for $C_{16}H_{17}I_3N_2O_6$: C 26.91; H 2.40; N 3.92.

TABLE 4

Starting materials (acid chlorides) used in the preparation of the Compounds of TABLE 1.

1. 3-N-methylacetamido-2,4,6-triiodobenzoyl chloride.
2. 3-N-n-butylacetamido-2,4,6-triiodobenzoyl chloride.
3. 3-amino-5-N-methylacetamido-2,4,6-triiodobenzoyl chloride.
4. 3-diacetylamino-5-N-methylacetamido-2,4,6-triiodobenzoyl chloride.
5. 3-acetamido-5-N-methylacetamido-2,4,6-triiodobenzoyl chloride.
6. 3-N-($\beta$-acetoxyethyl)-acetamido-5-N-methylacetamido-2,4,6-triiodobenzoyl chloride.
7. N,N'-di-($\beta$-acetoxyethyl)-3,5-diacetamido-2,4,6-triiodobenzoyl chloride.
8. 3-acetamido-5-N-methylcarbamyl-2,4,6-triiodobenzoyl chloride.
9. 3-acetamido-5-acetamidomethyl 2,4,6-triiodobenzoyl chloride.
10. N-methyl-3-butyramido-2,4,6-triiodobenzoyl chloride.
11. 5-acetamido-2,4,6-triiodoisophthaloyl chloride.
12. 5-diacetylamino-2,4,6-triiodoisophthaloyl chloride.
13. 3,5-bis-(diacetylamino)-2,4,6-triodobenzoyl chloride.
14. 3,3'-(adipoyldiimino)-bis-(2,4,6-triiodobenzoyl chloride.
15. 3-diacetylamino-2,4,6-triiodobenzoyl chloride.
16. 3-N-methylacetamido-5-N-(2,3-diacetoxypropyl)-acetamido-2,4,6-triiodobenzoyl chloride.

TABLE 5

Preparation of starting materials of TABLE 4

Analysis: found / calc.

| Starting material No: | m.p. °C | Yield % | C% | H% | H% | Cl% | I% | Prepared by a method analogous to Preparation No. |
|---|---|---|---|---|---|---|---|---|
| 1 | 162–167 | 78 78 | | | | 6.04 6.02 | | 1 |
| 2 | 91–118 | | 25.13 24.73 | 1.98 2.08 | 2.71 2.22 | 5.51 5.62 | 59.9 60.3 | 1 |
| 3 | 181–205 | 91 | | | | 5.37 5.88 | | 1* |
| 3 | | 87 | | | | 5.78 5.88 | | 2* |
| 4 | 261–265 | 85 | 24.84 24.43 | 2.12 1.76 | 4.10 4.07 | 5.20 5.15 | | 3a* |
| 5 | 238–240 | 66 | | | | 5.41 5.49 | | 3b* |
| 6 | 183–186 | 82 | 26.26 26.23 | 2.38 2.20 | 4.03 3.82 | 4.80 4.84 | | ¼* |
| 7 | 153–160 | 82 | | | | 4.40 4.43 | | ¼ |
| 8 | about 265 de-comp | 66 | | | 4.82 4.43 | 5.05 5.61 | 59.9 60.20 | 1 |
| 9 | 225 de-comp | 52 | | | | 5.46 5.49 | | 1 |
| 10 | 135–137 | 72 | 23.33 23.34 | 1.73 1.80 | 2.36 2.27 | 5.76 5.74 | 58.79 61.66 | 1$^a$ |
| 11 | 219–230 (dec) | 65 | 18.84 18.84 | 0.67 0.63 | 2.60 2.20 | | 58.90 59.70 | 3b |
| 12 | 170–180 | 60 | 21.04 21.20 | 1.10 0.89 | 2.48 2.06 | 10.20 10.43 | 55.00 56.01 | 3a |
| 13 | 220–235 | 86 | | | 3.67 3.91 | 4.93 4.95 | | 1 |
| 14 | 308–318 (dec) | 89 | | | | 5.64 6.03 | | 1 |
| 15 | 159–165 | 89 | | | | | | 1$^b$ |
| 16 | 125–127 | | | | | 4.45 4.41 | 46.30 47.32 | 1$^c$ |

Footnotes to Table 5:
*Compound features in the preparation cited
$^a$Initial starting material prepared by N-methylation of 3-butyramido-2,4,6-triiodobenzoic acid according to British Patent No. 987,796.
$^b$The corresponding 3-diacetylamino-2,4,6-triiodobenzoic acid was prepared from 3-acetamido-2,4,6-triiodobenzoic acid by treatment with wet acetic anhydride at 80° C
$^c$The corresponding O-acetylated acid was prepared by acetylation of 3-N-methylacetamido-5-N-(2,3-dihydroxy-propyl)-acetamido-2,4,6-triiodobenzoic acid by a method analogous to Preparation 4.

The starting materials illustrated in Table 5 were used in the preparation of the X-ray contrast agents given in Table 1. Table 6 lists the method used and experimental details with reference to the following preparations which illustrate specimen methods used. The actual method used in any one example may vary slightly in inessential features.

Preparations b. Compounds of TABLE 1

5. N-(3-N-methylacetamide-2,4,6-triiodobenzoyl)-glucamine

The acid chloride from Preparation 1 (12 g., 0.02 mole) was dissolved in dioxan (120 ml.). To the solution was added water (25 ml) and NaHCO$_3$ (1.9 g, 0.022 mol). Glucamine (4.0 g, 0.022 mol) was added in portions and the reaction mixture left by stirring at room temperature for 24 hours. The solution was evaporated to dryness in vacuo, the residue dissolved in water (500 ml), filtered clear and run through an Amberlite IR 120 H$^+$ ion exchange column. The effluent was evaporated to dryness in vacuo resulting in a white crystalline residue. Yield: 11.7 g (80 %); m.p. 100° – 120° C. The product was crystallised from isopropanol (charcoal-treated when in solution), dissolved in water and charcoal-treated at 100° C for 20 min. The water was distilled off in vacuo and the white residue dried in vacuo at 70° C; m.p. 120°–130° C.

Found: C 26.34; H 3.05; N 3.95; I 51.4. Calcd. for C$_{13}$H$_{21}$I$_3$N$_2$O$_7$; C 26.17; H 2.83; N 3.82; I 51.87.

6. N-(3-diacetylamino-5-N-methylacetamide-2,4,6-triiodo benzoyl)-N-methylglucamine Acid chloride from Preparation 3(a)(41.4 g, 0.06 mol) was dissolved in dioxan (750 ml). To the solution were added water (150 ml) and KHCO$_3$ (6.6 g, 0.066 mol) by stirring at room temperature. N-methylglucamine (12.9 g, 0.066 mol) was added in portions. After stirring for 20 hours the solution was evaporated to dryness in vacuo, the residue was dissolved in water (400 ml) at 50° C, filtered clear, pH adjusted to 1 and charcoal-treated at room temperature for 16 hours, filtered the filtrate was extracted with phenol (4 × 50 ml), the phenol was washed with water (4 × 40 ml) and diluted with ether (600 ml), the phenol/ether was extracted with water (4 × 50 ml) and the combined aqueous layer was washed with ether (3 × 30 ml) and evaporated to dryness in vacuo.

Yield: 38.3 g (75%); m.p. 115°–126° C. The product was crystallized from isopropanol (charcoal-treated when in solution), dissolved in water, charcoal-treated at 60° C, the filtrate evaporated to dryness and the purified product dried in vacuo at 70° C. M.p. 155° – 165° C.

Found: I 44.2 Calcd. for $C_{21}H_{28}I_3N_2O_9$: I 44.93.

7. N-(N-methyl-3,5-diacetamido-2,4,6-triiodobenzoyl)-N-methylglucamine

The triacetyl derivative of Preparation 6 (29 g) was hydrolysed by dissolving it in water at 60° and adding 2N sodium hydroxide solution in drops at pH 10 – 11 until the pH stabilised at 10.8. At room temperature the pH was adjusted to 1, the solution charcoal-treated for 1 hour, filtered and extracted with phenol etc. as described in Preparation 6 (4 × 40 ml phenol, 3 × 30 ml water, 350 ml ether, 4 × 50 ml water and 2 × 25 ml ether). It was isolated 25.8 g (91%); m.p. 110°–130° C. The product was purified as described in Preparation 6. M.p. 165° – 170° C. $[\alpha]_D^{20}$ — 4.5° (c 10% in 0.1 N HCl;

Found: C 28.38; H 3.53; N 5.49; I 47.1. Calcd. for $C_{10}H_{26}I_3N_3O_8$: C 28.34; H 3.26; N 5.22; I 42.29.

8. N-[3-N (β-Hydroxyethyl)-acetamido-5-N-methylacetamido-2,4,6-triiodobenzoyl]-N-methyl-2,3,-dihydroxypropylamine 3-N-(β-acetoxyethyl)-acetamido-5-N-methylacetamido-2,4,6-triiodobenzoyl chloride (28.3 g, 0.04 mol) was dissolved in dioxan (280 ml). Water (60 ml) and $KHCO_3$ (4.4 g, 0.044 mol) were added by stirring. To this solution N-methyl-2,3-dihydroxypropylamine (4.63 g, 0.044 mol) dissolved in dioxan (5 ml) was added in drops at room temperature in the course of 15 min. The stirring was continued for 16 hours. The solution was evaporated to dryness, the residue dissolved in water (200 ml), filtered clear, the solution heated to 60° C and 2N sodium hydroxide solution was added in drops (pH 10 – 11) until the pH became stable at 10.5. At pH 1 the solution was charcoal-treated for 1 hour at room temperature. The filtrate was evaportated with phenol as described previously. The final aqueous solution was charcoal-treated at room temperature for 16 hours and evaporated to dryness.

Yield: 25.5 g (84%), m..p. 140°–145° C. Found: C 28.70%: h 3.75%; N 5.45%; I 50.3%. Calc. for $C_{18}H_{24}I_3N_3O_6$: C 28.51; H 3.19; N 5.54; I 50.2.

9. 3,5-Bis[N-(2',3'-dihydroxypropyl)-N-methylcarbamoyl]-N-(2'-hydroxyethyl)-2,4,6-triiodacetanilide.

3,5-Bis[N-(2', 3'-dihydroxypropyl)-N-methylcarbamoyl]-2,4,6-triiodescetanilide (3.9 g; 5 m mole) was dissolved in water (8 ml) and then 5N sodium hydroxide (3 ml) and 2-chloroethanol (0.67 ml; 10 m mole) were added. After two days at room temperature, the solution was acidified with 6N hydrochloric acid and evaported to dryness in vacuo. The residue was dissolved in water (15 ml) and extracted with phenol (4 × 5 ml), the combined phenol extracts washed with water, and diluted with ether (60 ml). This phenol-ether mixture was extracted with water (4 × 10 ml) which was finally washed with ether. Then the aqueous solution was evaporated in vacuo to dryness. Yield: 1.6 g (40%). Melting point: 146°–159°. (Found: C 29.26; H 3.67; I 46.2; N 5.08. Calcd. for $C_{20}H_{28}I_3N_3O_8$: C 29.32; H 3.45; I 46.47; N 5.13).

TABLE 6

Preparation of compounds of TABLE 1

Analysis: found / calc.

| Compound No: | m.p. °C | Yield % | C% | H% | N% | I% | Prepared analogously to preparation No: | Starting Material No: |
|---|---|---|---|---|---|---|---|---|
| 1 | 120–130 | 80 | 26.34 / 26.17 | 3.05 / 2.83 | 3.95 / 3.82 | 51.4 / 51.87 | 5 * | 1 |
| 2 | 155–165 | 75 | | | | 44.20 / 44.93 | 6 * | 4 |
| 3 | 165–170 | 91 | 28.38 / 28.34 | 3.53 / 3.26 | 5.49 / 5.22 | 47.10 / 42.29 | 7 *ab | — |
| 4 | 140–145 | 84 | 28.70 / 28.51 | 3.75 / 3.19 | 5.45 / 5.54 | 50.30 / 50.20 | 8 * | 6 |
| 5 | 113–123 | 95 | 28.55 / 28.92 | 3.48 / 3.32 | 5.44 / 5.33 | 47.70 | 6 | 7 |
| 6 | 176–188 | 80 | 27.56 / 27.33 | 3.26 / 3.06 | 5.12 / 5.31 | 47.20 / 48.11 | 6 c | 8 |
| 7 | 149–152 | 51 | 28.22 / 28.34 | 3.44 / 3.25 | 5.06 / 5.22 | 47.70 / 47.29 | 6 d | 9 |
| 8 | 58–84 dec | 70 | 28.80 / 29.40 | 3.87 / 3.51 | 3.56 / 3.61 | 47.60 / 48.18 | 6 | 10 |
| 9 | 135–159 | 39 | 28.29 / 27.89 | 3.52 / 3.12 | 5.60 / 5.42 | 48.50 / 49.11 | 6 | 11 |
| 10 | 218–225 (dec) | 88 | 28.81 / 28.83 | 3.44 / 3.15 | 4.95 / 5.05 | 45.40 / 45.69 | 8 e | 6 |
| 11 | 230 (dec) | 78 | 27.37 / 27.39 | 3.09 / 2.81 | 5.35 / 5.33 | 47.85 / 48.25 | 6 | 4 |
| 12 | 195–205 | 83 | | | 4.82 / 4.87 | 43.80 / 44.11 | 8 f g | 7 |
| 13 | 78–89 | 69 | 31.04 / 30.40 | 3.73 / 3.70 | 3.72 / 3.55 | 48.80 / 49.05 | 5 | 2 |
| 14 | 260–270 (dec) | 41 | 26.30 / 20.33 | 2.77 / 2.61 | 5.47 / 5.42 | 48.7 / 49.12 | 7 | 13 |
| 15 | 190–195 | 77 | 26.90 / 27.33 | 3.19 / 3.06 | 5.39 / 5.31 | 47.9 / 48.12 | 7 h | 4 |
| 16 | 279–285 | 84 | 26.18 / 26.29 | 2.86 / 2.85 | 5.10 / 5.41 | 48.70 / 48.98 | 7 | 13 |
| 17 | 275– | 46 | 25.87 | 3.17 | 5.20 | 48:70 | 7 | 13 |

TABLE 6-continued

Preparation of compounds of TABLE 1

Analysis: $\left.\begin{array}{c}\text{found}\\\text{calc.}\end{array}\right)$

| Compound No: | m.p. °C | Yield % | C% | H% | N% | I% | Prepared analogously to preparation No: | Starting Material No: |
|---|---|---|---|---|---|---|---|---|
|  | 305 |  | 26.29 | 2.85 | 5.41 | 48.98 |  |  |
| 18 | 146–159 | 40 | 29.26 / 29.32 | 3.67 / 3.45 | 5.08 / 5.13 | 46.20 / 46.47 | 9 *ⁱ | — |
| 19 | 258–300 (dec) | 18 | 26.32 / 26.34 | 2.60 / 2.60 | 5.37 / 5.42 | 49.10 / 49.11 | 5 ʲ | 8 |
| 20 | 228–251 | 40 | 25.66 / 26.27 | 2.91 / 2.85 | 5.66 / 5.41 | 48.20 / 48.99 | 5 ᵏ | 8 |
| 21 | 264–270 | 84 |  |  | 6.32 / 5.41 | 46.70 / 48.99 | 6 ˡ | 8 |
| 22 | 182–240 (dec) | 77 | 28.36 / 27.86 | 3.18 / 2.95 | 4.96 / 5.13 | 45.50 / 46.47 | 9 ᵐ | — |
| 23 | 145–181 | 55 | 27.49 / 27.79 | 3.28 / 3.19 | 5.26 / 5.12 | 46.70 / 46.36 | 9 ⁿ | — |
| 24 | 149–173 | 73 |  |  | 5.18 / 5.12 | 47.00 / 46.36 | 9 ᵒ | — |
| 25 and 26: see Preparations 10 and 11 below |  |  |  |  |  |  |  |  |
| 27(a) | 183–186 | 92 | 25.16 / 25.60 | 2.69 / 2.46 | 4.24 / 4.27 | 57.90 / 57.94 | 5 | 14 |
| 27(b) | 162–167 | 92 | 26.96 / 27.33 | 3.15 / 2.97 | 4.08 / 3.75 | 51.05 / 50.97 | 5 * | 14 |
| 28 and 29: see Preparations 15 and 16 below |  |  |  |  |  |  |  |  |
| 30 | 100–110 | 87 | 26.25 / 26.17 | 3.17 / 2.83 | 3.95 / 3.82 | 51.50 / 51.87 | 7 | 15 |
| 31 | 109–116 | 79 | 27.70 / 27.29 | 3.15 / 3.10 | 3.72 / 3.50 | 50.10 / 51.0 | 5 | 1 |
| 32 | 180–188 | 16 |  |  |  | 51.90 / 52.10 | 5 | 1 |
| 33 | 165–175 | 85 | 27.20 / 27.33 | 3.19 / 3.06 | 5.33 / 5.31 | 47.3 / 48.12 | 7 | 4 |
| 34 | 151–160 | 35 | 26.99 / 26.87 | 2.89 / 2.82 | 5.55 / 5.86 | 53.00 / 53.23 | 7 | 4 |
| 35 | 130–135 | 76 | 29.88 / 29.70 | 3.70 / 3.56 | 4.98 / 4.95 | 44.10 / 44.83 | 8 | 6 |
| 36 | 95–110 | 61 | 31.27 / 30.99 | 4.17 / 3.62 | 4.87 / 4.72 | 41.60 / 42.72 | 6 | 6 |
| 37 | 252–260 | 60 | 26.67 / 26.87 | 3.02 / 2.81 | 5.46 / 5.87 | 52.90 / 53.23 | 8 | 6 |
| 38 | 135–146 | 50 | 28.22 / 28.50 | 3.20 / 3.05 | 5.69 / 5.76 | 51.70 / 52.52 | 8 | 6 |
| 39 | 126–138 | 87 | 28.81 / 28.51 | 3.52 / 3.19 | 5.39 / 5.54 | 49.40 / 50.20 | 8 | 6 |
| 40 | 282–291 | 76 | 27.48 / 27.40 | 3.28 / 2.98 | 5.51 / 5.64 | 50.70 / 51.10 | 8 | 6 |
| 41 | 274–276 | 5 | 27.98 / 27.89 | 3.30 / 3.12 | 5.67 / 5.42 | 48.60 / 49.10 | 8 | 6 |
| 42 | 119–121 | 31 | 29.58 / 30.05 | 3.85 / 3.67 | 5.03 / 4.78 | 38.30 / 43.20 | 8 | 16 |
| 43 | 125–135 | 93 | 30.18 / 30.05 | 3.95 / 3.67 | 4.80 / 4.78 | 43.20 / 43.20 | 8 | 7 |
| 44 | 119–130 | 99 | 29.21 / 28.92 | 3.79 / 3.32 | 5.18 / 5.33 | 47.80 / 48.23 | 8 | 7 |
| 45 | 163–165 | 95 | 27.92 / 27.40 | 3.11 / 2.98 | 5.60 / 5.64 | 50.60 / 51.10 | 8 | 7 |
| 46 | 222–252 | 61 | 27.66 / 27.89 | 3.22 / 3.12 | 5.10 / 5.42 | 48.90 / 49.11 | 6 | 11 |
| 47 | 313–321 | 72 | 25.82 / 25.72 | 2.50 / 2.70 | 5.38 / 5.62 | 50.30 / 50.95 | 6 | 11 |
| 48 |  |  |  |  |  | 47.30 / 48.25 | 6 ᵖ | 4 |
| 49 (=25) | 158– |  | 27.05 | 3.04 | 5.41 | 47.80 | 6/7 | 13 |

TABLE 6-continued

Preparation of compounds of TABLE 1

| Compound No: | m.p. °C | Yield % | C% | H% | N% | I% | Prepared analogously to preparation No: | Starting Material No: |
|---|---|---|---|---|---|---|---|---|
| | 166 | | 27.32 | 3.07 | 5.31 | 48.11 | | |

Footnotes for Table 6.
\* Compound featured in preparation cited
*a* the starting material was Compound No. 2
*b* $[\alpha]_D^{20} - 4.5°$ (C 10% in 0.1N HCl)
*c* $[\alpha]_D^{20} - 2.8°$ (C 10% in 0.1N HCl)
*d* $[\alpha]_D^{20} - 5.8°$ (C 10% in 0.1N HCl)
*e* $[\alpha]_D^{20} + 14.0°$ (C 10% in 0.1N HCl equilibrated with respect to mutarotation)
*f* $[\alpha]_D^{20} + 13.4°$ (C 10% in 0.1N HCl equilibrated with respect to mutarotation)
*g* triethanolamine used as base.
*h* $[\alpha]_D^{20} + 9.8$ (C 10% in 0.1N HCl)
*i* Compound No. 9 was used as starting material
*j* Solubility in water at 28° 1.4% (w/v)
*k* $[\alpha]_D^{20} + 7.0°$ (0.1N HCl)
*l* $[\alpha]_D^{20} - 2.5°$ (0.1N HCl)
*m* Compound No. 19 was used as starting material;
  $[\alpha]_D^{20} + 15.2°$ (0.1N HCl)
*n* Compound No. 20 was used as starting material;
  $[\alpha]_D^{20} + 7.8°$ (0.1N HCl)
*o* Compound No. 21 was used as starting material;
  $[\alpha]_D^{20} - 2.8°$ (0.1N HCl)
*p* $[\alpha]_D^{20} - 10.9°$ (0.1N HCl);
*q* $[\alpha]_D^{20} - 0.9°$ (c 5% in methanol)

Further Preparations

10. N-(3,5-Diacetamido-2,4,6-triiodobenzoyl)-N-methylglucamine a. N-(3,5-dinitrobenzoyl)-N-methylglucamine N-Methylglucamine (21.4 g, 0.11 mol) was suspended in DMF (200 ml). Triethylamine (11.5 g, 0.11 mol) was added. To this suspension was at 4° added by stirring 3,5-dinitrobenzoyl chloride (23.0 g, 0.1 mol) dissolved in dioxane (100 ml). The temperature rose to 10°. The stirring was continued at this temperature for 2 hours followed by 16 hours at room temperature. Triethylamine hydrochloride was filtered off and the DMF distilled off from the filtrate. The residue, a pale brown oil, was dissolved in water (200 ml), the pH adjusted to 1 and the solution extracted with phenol according to standard procedure. The final aqueous solution was treated with charcoal at room temperature for 24 hours and the filtrate evaporated to dryness in vacuo. The residue — a pale brown oil — was further dried in vacuo at 65°. Yield: 25.5 g (65%). The IR-spectrum showed a characteristic carbonyl absorption band at 1670 — 1620 cm $^{-1}$. $R_f$ value: 0.55 – 0.6 (paper, n-BuOH: EtON: NH$_3$: H$_2$O= 4 : 1 : 2 : 1).

b. N-(3,5-Diamino-2,4,6-triiodobenzoyl)-N-methyl-glucamine

The product of stage (a) (7.78 g, 0.02 mol) was dissolved in methanol (150 ml) and hydrogenated at room temperature and 3 kg/cm$^2$ in the course of 16 hours. Catalyst 1 g 5% Pd/C. The catalyst was filtered off, the filtrate treated with charcoal at pH 2 and the methanol distilled of in vacuo. The residue — a pale yellow oil — was dissolved in water, acidified to pH less than 1 and treated with charcoal at room temperature. A paper chromatogram (n-BuOH : EtOH : NH$_3$ : H$_2$O = 4 : 1 : 2 : 1) showed the desired product with $R_f$ value 0.14. The filtrate was in the course of 15 minutes added a 3.75N NaICl$_2$-solution (17.6 ml, 3.3 eqv.). The iodinated product separted as a dark brown oil. The reaction mixture was left at 3°, the supernatant was decanted and the oil dried in high vacuo at room temperature. The oil crystallized during this procedure. Yield: 7.5 g (53%), m.p. 110°.

c. N-(3,5-Diacetamido-2,4,6-triiodobenzoyl-N-methylglucamine.

The product of stage (b) (3 g, 4.2 mmol) was suspended in acetic anhydride (30 ml). After stirring at room temperature for 1 hour, H$_2$SO$_4$ conc. (0.3 ml) was added. All material dissolved. The stirring was continued for 16 hours before the acetic anhydride was distilled off in vacuo. The oily residue was dissolved in N sodium hydroxide solution (100 ml) acidified to pH 1 with 6N hydrochloric acid, treated with charcoal at room temperature and the filtrate extracted with phenol. The final aqueous solution was evaporated to dryness in vacuo, and the residue-a greyish crystalline product was dried in vacuo at 70°. Yield: 0.9 g (27%), m.p. 145° – 165°. Recrystallised from methanol, m.p. 155° –167°.

This compound showed identical IR-spectrum and chromatograhic data when compared with compound 49 of Table 6 which was prepared by reacting starting material 13 with N-methyl-glucamine.

11. N-(2,4,6-triiodobenzoyl)-N-methylglucamine a. 2,4,6-Triiodobenzoyl chloride 2,4,6-Triiodobenzoic acid (15 g) was suspended in thionyl chloride (75 ml) was refluxed. Thirty minutes after the starting material was dissolved, the reaction solution was cooled and evaporated in vacuo. The residue was dissolved in hot benzene (40 ml), cooled to room temperature, filtered and the filtrate evaporated in vacuo. Yield: 13.6 g. I.R. (KBr): 1785 cm $^{-1}$ (—COCl).

b. N-(2,4,6-Trioodobenzoyl)-N-methyl glucamine.

2,4,6-Triiodobenzoyl chloride (13.6 g; 26.2 mmole) was dissolved in DMF (30 ml) and cooled in ice-water. Potassium carbonate (4.0 g; 29 mmole) was added with stirring and then N-methyl-glucamine (5.65 g; 29 mmole) added during ninety minutes. After four hours, the temperature was allowed to rise to room temperature. After two days, the suspension was filtered and the filtrate evaporated in vacuo. The residue was dissolved in water (75 ml) and pH adjusted to about 0.5 – 1.0 with hydrochloric acid. The acidification involved a precipitation of a gum, which crystallized when treated with methanol. Finally the product was suspended in water (25 ml) for two hours. Yield: 11.7 g (66%. Melting point: 178° – 190°. IR (KBr): 1620 cm$^{-1}$ (CON ), broad band at 3300 cm$^{-1}$ (OH). (Found: C 24.17; H 2.75; I 57.0; N 2.26; Calc. for $C_{14}H_{18}I_3NO_6$: C 24.84; H 2.68; I 56.28; N 2.07.)

Preparation 12

3,5-Bis-[N-(2,3-dihydroxypropyl)-N-methylcarbomoyl]-2,4,6-triiodoacetanilide (Compound 9)

Acid chloride No. 11 from Table 4 (3.2 g, 0.005 mol) was dissolved in dimethylformamide (10 ml) and cooled in ice-water. The potassium carbonate (1.52 g, 0.011 mol) was added by stirring. A solution of 3-methylaminopropanediol-2,3 (1.16 g, 0.011 mol) in dimethylformamide (85 ml) was added during 15 minutes. After 4 hours the temperature was allowed to rise to room temperature and the stirring continued for further 20 hours. The mixture was filtered, the filtrate evaporated to dryness in vacuo and the residue extracted with phenol in the usual way. The final aqueous solution was evaporated to dryness in vacuo to yield 1.5 g (39%) desired product. M.p. 60°–75° C dec. This product was dissolved in methanol (10% solution) and the solution diluted with isopropanol (2 times the volume), decanted from the precipitated coloured impurities and evaporated to dryness in vacuo. The residue was dissolved in water, treated with charcoal, evaporated to dryness in vacuo, redissolved in water, treated again with charcoal and the filtrate evaporated to dryness in vacuo. M.p. 135°–159°. Found: C 28.29; H 3.52; N 5.60; I 48.5. Calcd. for $C_{18}H_{24}I_3N_3O_7$: C 27.89; H 3.12; N 5.42; I 49.11.

13. N-(N-Methyl-3,5-diacetamido)-2,4,6-triiodobenzoyl)-glucosamine

Acid chloride from Preparation 3 (41.3 g, 0.06 mol) was reacted with glucosamine and hydrolysed as described for Compound 3 in Preparations 6 and 7. Yield 36.0 g (76%).

14. N-(N-Methyl-3,5-diacetamido-2,4,6-triiodobenzoyl)-glucosamine (second route)

N-Methyl-3,5-diacetamido-2,4,6-triiodobenzoyl chloride (32.3 g, 0.05 mol) was dissolved in DMF (300 ml) at 0° C. Traces remained undissolved. Potassium carbonate (13.8 g, 0.1 mol) and glucosamine hydrochloride (10.8g, 0.05 mol) were added. The suspension was stirred at 0° for 2 hours and then at room temperature for further 20 hours. Potassium carbonate (2.76 g, 0.02 mol) and glucosamine hydrochloride (2.15 g, 0.01 mol) were added and the stirring was continued at room temperature for 46 hours. Total reaction time: 68 hours.

Inorganic salts were filtered off and the filtrate evaporated to dryness in vacuo at 50° – 55°. The residue was dissolved in water (200 ml), acidified by means of hydrochloric acid to pH 1 and treated with charcoal at room temperature for 16 hours. The aqueous solution was extracted with phenol as described previously. The final aqueous extract (pH about 4) was treated with charcoal for 20 minutes at 80°. The pale coloured filtrate was evaporated to dryness in vacuo and the residue dried in vacuo at room temperature for 24 hours. Yield: 31.0 g (78%). M.p. 165° – 230° (Dec.) The crude product was mixed with 20% w/w filter aid (speeder) and extracted in a soxhlet apparatus with tetrahydrofuran for 20 hours. Yield: 65% The product was further purified by crystallisation from isopropanol, dissolved in water and treated with charcoal first for 3 hours at room temperature, then 30 minutes at 80° – 90° and finally for 16 hours at room temperature. The colourless aqueous solution was evaporated to dryness in vacuo and the white crystalline residue dried in vacuo first at room temperature and then at 70°. M.p. 230° (dec.) $[\alpha]D20 = 18.0°$ (C = 10% in 0.1 N HCl; equilibrated with respect to mutarotation).

Found: C 27.37; H. 309; N 5.35; I 47.85. Calcd: for $C_{18}H_{22}I_3N_3O_8$ : C 27.39; H 2.81; N 5.33; I 48.25.

Thin layer chromatography (Silica F, n-BuCH : $H_2O$ : AcOH = 100 : 50 : 22) revealed 15 – 20% endo isomer ($R_f$ 0.44) and 80 – 85% exo isomer ($R_f$ 0.68). confirmed by n.m.r.

15. N-(Iodomethanesulphenyl)-N-Methylglucamine.

a. Trimethylsilyl (TMS) derivative of N-methylglucamine

N-Methylglucamine (10 g, 0.05 mol) was suspended (partly dissolved) in dry freshly-distilled pyridine and cooled in an ice-bath. Trimethyl silylchloride (30 g, 0.28 mol) was added in portions so that the temperature did not rise above 20°– 25°. After 1 hour the reaction slurry was poured into ether (200 ml) and water (200 ml) and shaken; the ether layer was washed several times with water, dried and evaporated at 50°–60° to leave the oily per-trimethylsilyl ether containing a trace of pyridine. Yield: ca. 20 g (50%).

Equivalent weight: calculated 555; found; 600.

b. N-(Iodomethanesulphonyl)-methyl-per-trimethylsilylglucamine

Iodomethane sulphonylchloride (2.4 g, 0.01 mol) was dissolved in dimethoxyethane (20 ml) and stirred at 0°. A solution of per-TMS-methylglucamine (6 g. 0.011 mol) and triethylamine (1.5 ml) in dimethoxyethane (20 ml). The reaction was continued overnight and then poured into ether (100 ml) and water (100 ml).

The ether layer was separated, washed several times with water and evaporated under vacuum at 50°– 60° to yield 1g of syrupy product.

Analysis: Found: I 16.2%; Calcd. I 16.7% for $C_{23}H_{58}INO_7SSi_5$.

c. N-(Iodomethanesulphonyl)-N-methylglucamine.

The trimethylsilyl ether from Stage (b) was dissolved in methanol-water (50:50, ca. 100 ml) and sufficient 2N hydrochloric acid added to give pH 2 – 3. The mixture was stirred vigourously for 2 hours, then extracted three times with ether and then the product isolated by the phenol method described in Preparation (6)

Yield: 1 g. m.p. : 105°–106°. $[\alpha]_D^{20}$ — 10.6° (C 10% in 0 1N HCl equilibrated with respect to mutarotation).

Analysis: Found: C 23.93; H 4.68; N 3.44; I 32.5; Calcd. for $C_8H_{18}INO_7S$;C 24.07: H 4.55; N 3.51; I 31.8.

Thinlayer chromatography: Silica (Butanol 100 : acetic acid 22 : water 50) $R_f$=0.57 Silica (Butanol 100 : ammonia 7 : water 30) $R_f$ = C.10. Solubility: Very soluble in hot water, appr. 10% in cold water.

16. N-(Iodomethanesulphonyl)-diethanolamine.

Iodomethanesulphenylchloride (2.4 g, 0.01 mol) was dissolved in dimethoxyethane and stirred at 0°. A solution of diethanolamine (2.4 g. 0.023 mol) in dimethylformamide/water was added, and stirring continued 1 hour. The reaction was then poured into water and the aqueous solution evaporated to dryness. The residue was dissolved in water and the product obtained by the above phenol extraction. Evaporation of the aqueous solution finally obtained yielded 1 g of product as a sticky solid. This was recrystallized from a small amount of water. M.P. 99°.

Analysis: Found: C 19.42; H 4.01; N 4.64; I 41.04. Calcd. C 19.68; H 3.91; N 4.56; I 40.9 for $C_5H_{12}INO_4S$.

Thinlayer chromatography: Silica (Butanol 100 : acetic acid 22 : water 50) $R_f$ 0.72; Silica (Butanol 100 : ammonia 7 : water 30) $R_f$ 0.65; Solubility: Soluble in hot water, sparingly soluble in cold.

17. N-(3-Acetamido-5-N-methylcarbamoyl-2,4,6-triiodobenzoyl)-N-(2-hydroxyethyl)-glucamine 3-Acetamido-5N-methylcarbamoyl-2,4,6-triiodobenzoyl chloride (18,4 g; 29 m mole) was suspended in DMF (100 ml) and cooled in ice-water. Then potassium carbonate (4.6 ; 33 m mole) and N-(2-hydroxyethyl)-glucamine (8 g; 36 m mole) were added. The mixture was stirred vigorously. After four hours, the temperature was allowed to rise to room temperature. The mixture was stirred for two days and then filtered. The filtrate was evaporated in vacuo to dryness and the residue dissolved in water (50 ml). Then the aqueous solution was acidified with hydrochloric acid and extracted with phenol (4 × 25 ml). The combined phenol extracts were washed with water, then diluted with ether (300 ml) and extracted with water (5 × 30 ml). Finally, the aqueous layer was washed with ether (4 × 20 ml) and evaporated to dryness in vacuo.

Yield: 18.9 g (79 %).

The product was dissolved in 80% (v/v) aqueous methanol (180 ml) and stirred with Dowex anion exchange resin 1 × 4 (5 g). The next day pH was about 7.1. After filtration, Amberlite cation exchange resin IR 120 H (2 g) was added and the suspension stirred for two hours. pH of the solution was about 3.5. Then Dowex anion exchange resin (2.5 g) was added. After the mixture was stirred for several hours, pH increased to 6.1. After filtration, Amberlite IR 120 H (2 g) was added and the mixture stirred for about two hours. pH decreased to 4.4. Then Dowex anion exchange resin (2 g) was added, the mixture stired for two hours and filtered (Ph was about 6.1). The ion exchange resins were collected on a filter and washed with 80 % (v/v) aqueous methanol. The filtered solutions were combined and evaporated to dryness in vacuo. Yield: 15.7 g. The product was recrystallized from isopropyl alcohol (120 ml). Yield: 11 g. The product (10 g) was dissolved in water (10 ml) and extracted three times with a mixture of chloroform -butanol (60:40). Then the aqueous layer was evaporated to dryness in vacuo. The product was redissolved in water and evaporated to dryness in vacuo twice. Yield: 9.0 g. Melting point: 178°-190°. (Found: I 45.8. Calc. for $C_{19}H_{26}I_3N_3O_9$ : I 45.8. Calc. for $C_{19}H_{26}I_3N_3O_9$ : I 46.36).

We claim:

1. A non-ionic X-ray contrast compound of the formula

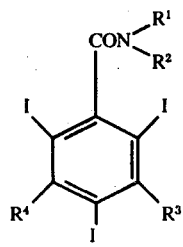

where $R^1$ and $R^2$, which may be the same or different, are each a hydrogen atom, an alkyl group, a hydroxylalkyl group or an alkanoyloxyalkyl group and $R_3$ and $R^4$, which may be the same or different, are each a group of the formula $-NR^5Ac$, where $R^5$ is a hydrogen atom, an alkyl group, a hydroxyalkyl group, an alkanoyloxyalkyl group or an alkanoyl group and Ac is an alkanoyl group; a group of the formula $-CH_2NR^5Ac$, where $R^5$ and Ac have the above meanings; or a group

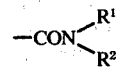

as defined above; each alkyl, hydroxyalkyl or alkanoyl group which is present having up to 6 carbon atoms there being at least one N-hydroxyalkyl and at least two hydroxyl groups in the molecule.

2. A compound as claimed in claim 1 in which at least one of $R^1$ and $R^2$ is an alkyl group or a hydroxyalkyl group.

3. A compound as claimed in claim 1 having at least one group of the formula $-NR^5Ac$ in which $R^5$ is a hydrogen atom, an alkyl group, a hydroxyalkyl group or an alkanoyloxyalkyl group.

4. A compound as claimed in claim 1 having at least one hydroxyalkyl group which is a β-hydroxyethyl, dihydroxypropyl or tris(hydroxymethyl-(methyl) group.

5. A compound as claimed in claim 1 selected from the group consisting of 3,5-bis-N-di-(β-hydroxyethyl)-carbamoyl-2,4,6-triiodoacetanilide; 3,5-bis-N-(2', 3'-dihydroxypropyl)-carbamoyl-2,4,6-triidoacetanilide; N-(3-N-methylacetamie-2,4,6-triiodobenzoyl)-glucamine; N-(3-diacetylamino-5-N-methylacetamido-2,4,6-triiodo-benzoyl)-N-methylglucamine; N-(N-methyl-3,5-diacetamide-2,4,6-triiodobenzoyl)-N-methyl glucamine; N-[3-N-(β-hydroxyethyl)-acetamido-5-N-methylacetamido-2,4,6--triiodobenzoyl]-N-methyl-2,3-dihydroxypropylamine; N-[N,N'-di-(β-hydroxyethyl)-3,5-diacetamido-2,4,6-triiodobenzoyl]-diethanolamine; 3-Acetamido-5-N-methylcarbamoyl-2,4,6-triidobenzoyl)-N-methylglucamine; N-(3-acetamido-5-acetamidomethyl-2,4,6-triiodeobenzoyl)-N-methylglucamine; 3,5-Bis[N-2,3-dihydroxypropyl)-N-methylcarbamoyl]-2,4,6-triiodoacetanilide; N-(N-methyl-3,5-diacetamido-2,4,6-triiodoenzoyl-2-glucamine; N-(3,5-diacetamido-2,4,6-triiodobenzoyl)-glucamine; N-(3,5-diacetamido-2,4,6-triiodobenzoyl)-2-glucamine; 3,5-Bis[N-2', 3'-dihydroxypropyl)-N-methylcarbamoyl]-N-2'-hydroxyethyl)-2,4,6-triiodoacetanilide; N-(3-acetamido-5-N-methylcarbamoyl-2,4,6-triiodobenzoyl)-D-2-glucamine; N-(3-acetamido-5-N-methylcarbamoyl-2,4,6-triiodobenzoyl)-D-1-glucamine; N-(3-β-hydroxyethylacetamido-5-N-methylcarbamoyl-2,4,6-triiodobenzoyl)-D-2-glucamine; N-(3N-β-hydroxyethylacetamido-5-N-methylcabamoyl-2,4,6-triiodobenzoyl)-D-1-glucamine; N-(3,5-diacetamido-2,4,6-triiodobenzoyl)-N-methyl-glucamine; N-(N-methyl-3,5-diacctamido-2,4,6-triiodobenzoyl)-D-glucamine; N-(N-methyl-3,5-diacetamido-2,4,6-triiodobenzoyl)-N,N-di-(β-hydroxyethyl)-amine; N-[3-N-methylacetamido-5-N-(β-hydroxyethyl)-acetamido- 2,4,6-triiodobenzoyl]-N-methylglucamine; N-[3-N-methylacetamido-5-N-(β-acetoxyethyl)-acetamido-2,4,6-triiodobenzoyl]-N-methylglucamine; N-[3-N-methylacetamido-5-N-(β-hydroxyethyl)-acetamido-2,4,6-triiodobenzoyl]-ethanolamine; N-[3N-methylacetamido-5-N-(β-hydroxyethyl)-acetamido-2,3,6-triiodobenzoyl]-N-methyethanolamine; N-[3-N-methlacetamido-5-N-(β-hydroxyethyl)acetamido-2,4,6 -triiodeobenzoyl]-diethanolamine; N-[3-N-methylacetamido-5-N-(β-hydroxyethyl)-acetamido-2,4,6-triiodobenzoyl]-N-(2,3,dihydroxypropyl)-amine; N-[3-N-methylacetamido-5-N-(β-hydroxyethyl)-acetamido-2,4,6-triiodobenzoyl]-N-[tris-(hydroxymethyl)-methyl]-amine; N-[3-N-methylacetamido-5-N-(2,3-dihydroxypropyl)-acetamido-2,4,6-triiodobenzoyl]-N-methylglucamine; N-[3-5-bis-N-(β-hydroxyethyl-acetamido-2,4,6-triiodobenzoyl-N-methyl-glucamine; N-[3,5-bis-N-(β-hydroxyethyl)-acetamido-2,4,6triiodobenzoyl]-N-methyl-N-(2,3-dihydroxypropyl-amine; N-[3,5-bis-N-(β-hydroxyethyl-acetamido-2,4,6 -triiodobenzoyl]-ethanolamine and N-[3-acetamido-5N-methylcarbamoyl-2,4,6-triiodobenzoyl]-N-(2-hydroxyethyl)-glucamine.

6. The compound of claim 1 which is N-(3-acetamido-5-N-methylcarbamoyl-2,4,6-triiodebenzoyl)-N-(2-hydroxyethyl)-glucamine.

7. The compound of claim 1 which is N-(3-acetamido-5-N-methylcarbamoyl-2,4,6-triiodobenzoyl)-N-methylglucamine.

8. The compound of claim 1 which is 3,5-bis-[N-(2,3-dihydroxypropyl)-N-methylcabamoyl]-2,4,6-triiodoacetanilide.

9. A non-ionic X-ray contrast compound which is N,N'-bis-[3-di-(β-hydroxyethyl)-aminocarbonyl-2,4,6-triiodophenyl]-adipamide or N,N'-bis-[3-(N-methyl)-glucaminocarbonyl-2,4,6-triiodophenyl]-adipamide.

* * * * *